United States Patent [19]

Thornton et al.

[11] Patent Number: 4,808,170

[45] Date of Patent: Feb. 28, 1989

[54] HYPOTRAUMATIC INJECTION NEEDLE USEFUL IN OPHTHALMIC SURGERY

[75] Inventors: Spencer P. Thornton; Rodger W. Williams, both of Nashville, Tenn.

[73] Assignee: Alcon Laboratories, Inc., Fort Worth, Tex.

[21] Appl. No.: 22,468

[22] Filed: Mar. 6, 1987

Related U.S. Application Data

[63] Continuation-in-part of Ser. No. 809,232, Dec. 16, 1985, abandoned.

[51] Int. Cl.$^4$ .............................................. A61M 5/32
[52] U.S. Cl. .................................................... 604/274
[58] Field of Search ................ 604/274, 272, 264, 239

[56] References Cited

U.S. PATENT DOCUMENTS 2,409,979 10/1946 Huber .................................... 604/274
3,064,651 11/1962 Henderson ........................... 604/274

OTHER PUBLICATIONS

Myers, "Topical Anesthesia and Soothing Explanation Better than Retrobulbar for Keratotomy", *Ocular Surgery News*, pp. 1 and 62 (Aug. 15, 1985).
Pannu, "Peribulbar Anesthesia Technique for RK", *Ocular Surgical News*, (Dec. 15, 1985).
Davis et al., "Posterior Peribulbar Anesthesia: An Alternative to Retrobulbar Anesthesia", *Cataract Refract. Surg.*, vol. 12, pp. 182–184 (1986).
O'Day, "RK Complications: Patients Need to be Told Facts Before Surgery", *Ophthalmology Times*, pp. 41–42 (Apr. 1, 1986).
Pautler et al., "Blindness from Retrobulbar Injection into the Optic Nerve", *Ophthalmic Surgery*, vol. 17, No. 6, pp. 334–337 (1986).
Gills, "Peribulbar Anesthesia: Report on 30,000 Cases", *Ocular Surgery News*, vol. 4, No. 13, pp. 22 and 35 (1986).
Kline, "Amaurosis Cases Prompt Changes in Retrobulbar", *Ocular Surgical News*, p. 23 (Jul. 1, 1986).
Bloomberg, "Periocular Technique Favored for Anesthesia: 4-cc Injections Given Superiorly, Inferiorly", *Ocular Surgery News*, pp. 22 and 24 (Jul. 1, 1986).
Brookshire et al., "Life-Threatening Complication of Retrobulbar Block", *Ophthalmology*, vol. 93, No. 11, pp. 1476–1478 (1986).
Javitt, "Potential for Complications Following Retrobulbar Anesthesia Justifies Anesthesiologist's Presence", *Ocular Surgery News*, pp. 19 and 41 (2-15-87).

*Primary Examiner*—John D. Yasko
*Attorney, Agent, or Firm*—James A. Arno; Gregg C. Brown

[57] ABSTRACT

A hypotraumatic injection needle having substantially no cutting edges is described. The injection needle has a beveled surface with the furthermost end of the beveled surface removed and rounded to form the needle tip. All edges on the tip and beveled portion of the needle are rounded and smoothly polished. The needle tip has a low profile, with the slope of the beveled portion being less than twenty degrees. These features allow the needle to penetrate easily by means of blunt dissection of tissue, rather than cutting tissue. The injection needle is particularly useful for posterior peribulbar or retrobulbar anesthesia in connection with ophthalmic surgery. The injection needle has a "ski-tip" effect, guiding the tip of the needle away from the beveled side. This effect, along with the absence of cutting edges, significantly reduces the hazards associated with ophthalmic surgical injections, such as inadvertent cutting of the eyeball or optic nerve. A preferred embodiment of the needle is indexed to indicate the side of the needle which is away from the beveled side.

6 Claims, 1 Drawing Sheet

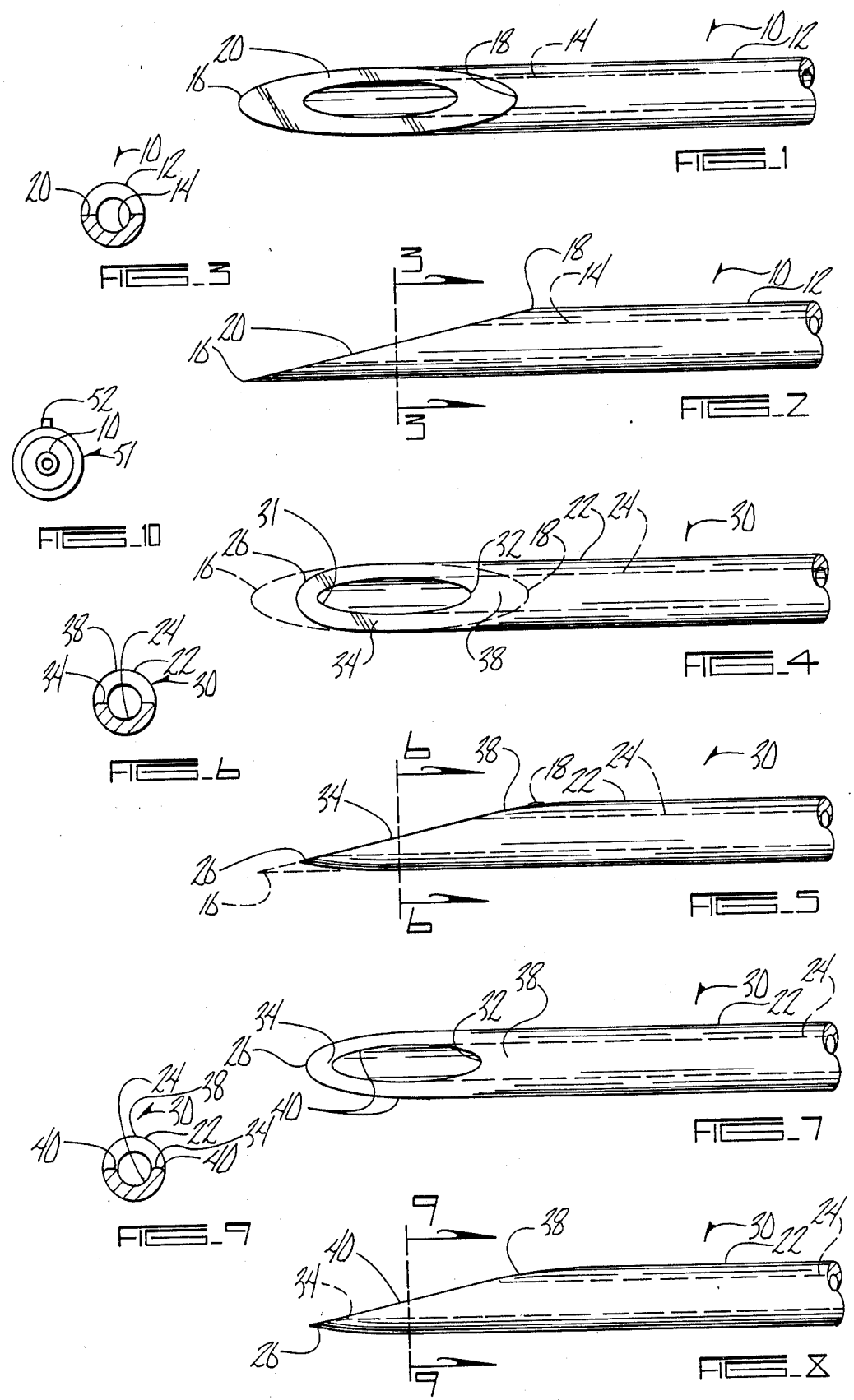

HYPOTRAUMATIC INJECTION NEEDLE USEFUL IN OPHTHALMIC SURGERY

CROSS-REFERENCE TO RELATED APPLICATION

This application is a continuation in-part of U.S. patent application Ser. No. 809,232, filed Dec. 16, 1985 now abandoned.

BACKGROUND OF THE INVENTION

Injection needles are known for injecting medication or anesthetic to a patient. The known injection needles generally are tubular hollow cylindrical bodies having a penetrating end. Such penetrating ends are generally formed by slicing the hollow tubular needle body at an angle. This provides a sharper, reduced area for breaking of the tissue to ease insertion of the needle. Reference is made to the following patents for further background information concerning the injection needles of the prior art: U.S. Pat. Nos. 2,409,979; 2,711,733; 2,717,600; 3,064,651; 3,071,135; and 3,093,134.

The present invention is concerned with the provision of hypotraumatic injection needles, particularly hypotraumatic injection needles adapted for use in ophthalmic surgery. In many opthalmic surgical procedures, such as cataract surgery, it is necessary to inject a local anesthetic in the orbit (i.e., eye socket) behind the globe (i.e., eyeball). This is a very delicate procedure, since a misplacement of the needle can result in serious damage to the eyeball and/or the optical nerve. Moreover, the anesthetic must be injected in a very specific location behind the eyeball in order to properly anesthetize the eyeball and adjacent tissue.

One of the hazards of injecting anesthesia behind the eyeball, which may also be referred to as a "retrobulbar" injection, is that the injection needle may severe or otherwise damage the optic nerve. Such damage to the optic nerve may result in a partial or total loss of vision of the eye, depending on the extent of the damage to the optic nerve.

Another hazard associated with retrobulbar injections is that the injection needle may inadvertently come into contact with the eyeball and cut ocular tissue. This is a significant hazard, because any cutting of ocular tissue creates a risk that an ocular infection will develop; moreover, a serious cut may directly damage the vision of the patient by, for example, injuring the cornea. The above-described hazard also exists in connection with other types of injections in and around the eye, which may be referred to as "peribulbar" injections.

SUMMARY OF THE INVENTION

It is an object of the present invention to provide a hypotraumatic, self-guiding injection needle which is substantially without cutting edges.

It is another object of the present invention to provide a self-guiding injection needle for peribulbar or retrobulbar injections.

The needle of the present invention is formed from a hollow tubular body having an end which is initially formed as the intersection of a plane at an angle to the axis of the hollow tubular body. The uppermost surface of the end of the tubular body is smoothly rounded about the truncation of the hollow tubular body, so that no sharp line is formed. Rather, a smooth transition is formed between the truncated potion of the needle end and the generally hollow cylindrical body. Furthermore, the sides of the tip are also smoothly rounded to provide a generally smooth transition, so that the needle has substantially no sharp edges capable of cutting tissue.

The configuration of the injection needle of the present invention produces a ski effect, guiding the tip of the needle away from the beveled side so that if the needle is placed with the bevel pointing toward, for example, the eyeball, the needle will be guided away from the eyeball, rather than into it. The elimination of cutting edges reduces the potential for vessel and nerve laceration and generally reduces the trauma to tissue contacted by the injection needle. Instead of cutting tissue, the injection needle of the present invention penetrates by separating tissue. This type of penetration may also be referred to as "blunt dissection." The blunt separation of tissue results from contact between tissue and the smooth rounded edges of the needle tip. In contrast, the conventional injection needles of the prior art have one or more sharp, flat surfaces which cut rather than separate tissue. The needle of the present invention is able to penetrate tissue easily because of its low profile. That is, the slope of the beveled portion of the needle is relatively flat, with the angle between a plane through the horizontal axis of the needle and a plane parallel to the slope of the beveled portion being less than twenty degrees (20°).

As a preferred embodiment of the present invention an indexing device on the hub of the needle identifies the back "away from the bevel" side and aids in properly positioning the needle before injection.

BRIEF DESCRIPTION OF THE DRAWINGS

The foregoing and other objects of this invention will be better understood by reference to the accompanying drawings, wherein:

FIG. 1 is a top elevational view of a standard retrobulbar needle;

FIG. 2 is a side elevational view of the needle of FIG. 1;

FIG. 3 is a sectional view taken along lines 3—3 of FIG. 2;

FIG. 4 is a top elevational view showing modifications to the prior art retrobulbar needle;

FIG. 5 is a side elevational view of the needle of FIG. 4;

FIG. 6 is a sectional view taken along lines 6—6 of FIG. 5;

FIG. 7 is a top elevational view of the needle according to the present invention;

FIG. 8 is a side elevational view of the needle of FIG. 7;

FIG. 9 is a sectional view taken along line 9—9 of FIG. 8; and

FIG. 10 is a front elevational view of a needle according to the present invention which includes an indexing means.

DETAILED DESCRIPTION OF THE INVENTION

A prior art hollow tubular needle 10 is seen in FIG. 1 as having an elongated hollow tubular body 12 with an interior passageway 14. The needle 10 has a truncated surface 20, having a furthermost, distal end 16 and a near end 18.

The surface 20 of the prior art needle 10 is planar as seen in FIG. 2. The tip 16 of the needle 10 is located at the lowermost surface of the body 12.

The sectional view of FIG. 3 of the prior art needle 10 clearly shows the level lines indicating the lowermost edge of the surface 20 where it intersects the vertical section taken along lines 3—3 of FIG. 2. As seen in FIG. 3, the body 12 is generally tubular with the passageway 14 formed therein concentrically.

FIG. 4 shows modifications to the prior art needle of FIG. 1, exaggerated somewhat for clarity. In FIG. 4, the original needle shape is indicated in dotted outline, having a phantom tip 16 indicated. Also, a phantom beveled region 38 is shown. In the modification of FIG. 4, the truncated surface 34 is polished in the region 38 to round the region nearest the portion 18.

As seen in FIG. 4, the modified needle has a new tip 26, a generally beveled surface 34, and interior passageway ends 31 and 32. The interior passageway 24 of the modified needle 30 is formed in a generally tubular body 22, as seen in FIG. 4.

The formation of the new tip 26 of the modified needle 30 is seen in FIG. 5, as being formed from removal of a substantial portion of the tip 16 of the prior art needle. A lowermost rounded surface 36 is seen adjacent the tip 26 of the needle 30 of FIG. 5. The rounded, polished region 38 is seen at the uppermost, rightmost region of the beveled portion 34.

The beveled region 38 is seen indicated in FIG. 6, which is a sectional view taken along lines 6—6 of FIG. 5. In this view, the intersection of the beveled portion 34 with the sectional view of the body 22 is at a generally horizontal line. Thus, it is seen in FIG. 6 that the outermost edges of the intersection of the bevel 34 with the body 22 is relatively sharp and such edges could readily tear or cut into tissue as the needle 30 is moved during an operation within tissue, particularly when it is moved within eye tissue and tissue surrounding the eyes.

The needle 30 of FIG. 7 illustrates the final needle configuration of the present invention, having all sharp edges rounded and polished. Side edges 40 are rounded by being smoothly polished around the region of the truncation formed by the beveled surface 34. The region 38 blends smoothly with the body 22 of the needle 30 so that no sharp line nor flat surface is formed or seen in FIG. 7.

The side elevational view shown in FIG. 8 is similar to the side elevational view shown in FIG. 5, with the rounded edges being shown as region 40 in FIG. 8.

As seen in FIG. 9, the outermost edges 40 are rounded, and the rounded regions 40 blend smoothly with the body 12 so that no sharp cutting edges are formed by the edges 40. The region 38 is indicated in FIG. 9, and is located similarly to the location shown in FIG. 6.

The final article shown in FIGS. 7-9 illustrates a self-guiding, hypotraumatic injection needle 30 for posterior peribulbar or retrobulbar injections, which is substantially without cutting edges. The needle 30 tapers to a rounded and polished tip 26 located at the forward end of the needle 30. The beveled surface 34 with its smooth, rounded edges produces a "ski tip" effect, guding the tip of the needle away from the beveled or slanted side 34, so that if the needle is placed with the beveled surface 34 pointing toward the eyeball, the needle 30 will be guided away from the eyeball, rather than into it. The reduction or elimination of cutting edges, as seen by the rounded regions 36, 38 and 40, reduces the potential of vessel and nerve laceration.

As shown in FIG. 10, an indexing means 50 can be placed on the hub of the needle to identify the portion of the needle 30 which is away from the beveled side 34. The indexing means aids in properly positioning the needle 30 before injection. Any indexing means can be used, for example, a notch on the side or hub of the needle can be formed, which is located corresponding to a region away from the beveled side 34. Alternatively, the indicator can also indicate the side which is toward the bevel 34, that is, which is nearest the region 38 of the needle 30. Other indexing means may also be used, such as providing a raised dot 52 on the needle hub 51, as shown in FIG. 10, or any other indicating means.

The low profile, smooth edged configuration of the needle 30 permits the needle 30 to virtually glide through tissue, self-directing the needle 30 away from the beveled surface 34, similar to the way in which a ski moves through snow, with the tip 26 being directed away from any unwanted obstacles (e.g., the eyeball).

Use of the inventive needle 30 ensures maximum safety to the eyeball and to the optic nerve. The needle may be used for superior and/or inferior injections. These injections may be performed, for example, by inserting the needle 30 just below the upper orbital rim or above the lower orbital rim approximately at the mid-line and passing the needle almost straight back as far as it will go with the beveled side 34 away from the globe until it reaches the posterior orbital wall. The needle 30 should not be directed into the muscle cone, nor should it be directed toward the thin orbital roof. Avoiding injection into the muscle cone also avoids respiratory depression and meningial irritation and avoids total blackout during surgery.

The needle of the present invention is capable of accomplishing all of the above-enumerated objects and advantages, and while a preferred embodiment has been shown and illustrated, it is not limited thereto, but is embodied within the scope of the following claims.

What is claimed is:

1. A self-guiding, hypotraumatic, ophthalmic injection needle adapted for retrobulbar and peribulbar injections, comprising:

a tubular body having a first end, a second end, and a longitudinal axis extending between the first end and the second end, said first end comprising a penetrating end;

said penetrating end including a generally planar beveled surface which substantially truncates the tubular body at an angle relative to the longitudinal axis of the tubular body, and a tip portion located at the forward most point of the first end;

said beveled surface having a configuration of a generally elliptical ring, and including an outer periphery and an inner periphery, all portions of said beveled surface including said inner periphery and said outer periphery being polished and smoothly rounded to eliminate all cutting edges;

said tip portion having a first region which joins the tip portion to the tubular body, said first region being rounded and polished such that the tip portion curves toward the beveled surface.

2. An ophthalmic injection needle according to claim 1, wherein the needle penetrates tissue by means of blunt dissection and travels away from the beveled surface during penetration of tissue.

3. An ophthalmic injection needle according to claim 1, wherein the beveled surface truncates the tubular body at an angle of less than 20°.

4. An ophthalmic injection needle according to claim 1, further comprising an indexing means on the second end of the tubular body, said indexing means positioned on the side of the tubular opposite from the beveled surface of the penetrating end.

5. An ophthalmic injection needle according to claim 4, wherein the indexing means comprises a projection on the second end of the tubular body.

6. An ophthalmic injection needle according to claim 4, wherein the indexing means comprises a projection on a hub attached to the second end of the tubular body.

* * * * *